United States Patent [19]

Zissimopoulos

[11] 4,214,237

[45] Jul. 22, 1980

[54] ELECTRICAL INDICATOR MEANS FOR INDICATING THE CORRECT POSITION OF A CASETTE IN FLOW CONTROLLING

[75] Inventor: Nicholas Zissimopoulos, Schaumburg, Ill.

[73] Assignee: Baxter Travenol Laboratories, Inc., Deerfield, Ill.

[21] Appl. No.: 12,989

[22] Filed: Feb. 21, 1979

[51] Int. Cl.² .................. G07F 11/60; G08B 21/00
[52] U.S. Cl. .................. 340/686; 137/554; 200/61.58 R; 200/61.85; 221/4; 221/197; 222/41; 222/325
[58] Field of Search ............... 340/686, 673; 200/61.58, 61.85; 222/41, 46, 47, 44, 23, 325, 450; 221/4, 197, 198, 312 C; 116/230, 286, 315; 137/554, 555; 141/94; 209/546, 549, 909; 360/93, 96.5, 96.6

[56] References Cited

U.S. PATENT DOCUMENTS

| | | | |
|---|---|---|---|
| 3,029,418 | 4/1962 | Clinton | 200/61.58 R X |
| 3,120,324 | 2/1964 | Amberg et al. | 221/4 |
| 3,636,273 | 1/1972 | Lemelson | 360/93 |
| 3,807,467 | 4/1974 | Tascher et al. | 222/325 X |
| 3,870,247 | 3/1975 | Carisey | 360/96.6 X |
| 4,028,735 | 6/1977 | Miyazaki | 360/93 X |
| 4,121,584 | 10/1978 | Turner et al. | 222/450 X |

Primary Examiner—John W. Caldwell, Sr.
Assistant Examiner—Joseph E. Nowicki
Attorney, Agent, or Firm—Paul C. Flattery; John P. Kirby; John A. Caruso

[57] ABSTRACT

Flow controlling apparatus for the administration of parenteral solutions or the like includes a casette in a controller member adapted to receive and hold the casette. In accordance with this invention, means are provided for indicating the correct position of the casette in the controller member.

6 Claims, 6 Drawing Figures

ELECTRICAL INDICATOR MEANS FOR INDICATING THE CORRECT POSITION OF A CASETTE IN FLOW CONTROLLING

BACKGROUND OF THE INVENTION

In U.S. Pat. No. 4,121,584 of Turner, et al., a technique for the positive control of flow of parenteral solution or the like is provided, utilizing only the gravity head pressure of the solution, coupled with excellent accuracy of delivery volume. The flow control device utilizes a pair of alternating valves which open and close, controlling the inlet and outlet of a metering chamber.

In the patent application of Nicholas Zissimopoulos, Ser. No. 878,970, filed Feb. 17, 1978, an improved system is disclosed for a flow control device, utilizing the principles disclosed in the Turner, et al. patent. Specifically, a separable casette defining a fluid flow path through it and having valvable inlet and outlet means is provided for temporary installation in a controller. The controller provides means for valving the inlet and outlet in the manner desired for administering a predetermined flow volume of fluid through the casette.

Accordingly, the casette may be part of a disposable solution administration set, while the controller constitutes permanent equipment.

As shown in the cited patent and application, the valving means comprises a pair of plungers, as part of the controller, which penetrate apertures in the casette and press a membrane against the walls of orifices at the inlet and the outlet of a metering chamber. This provides reliable metering of liquid through the casette.

Since the casette should be installed in the controller with the plungers penetrating through apertures into the casette, the above-cited patent application provides mechanical means for installation of the casette into its proper position. This is accomplished by sliding the casette into a holding bracket which precisely positions it, and then rotating a crank which moves the casette laterally into engagement with the plungers.

While the previously described device permits the reliable engagement of the casette into its proper position, it is desirable for a clear visual and/or auditory alarm signal to be provided to indicate the proper engagement of the casette, to avoid any remote possibility of the apparatus being inoperative during use because of the accidental failure to properly move the casette laterally into completely engaged position by use of the crank.

In accordance with this invention, such an alarm system is provided so that a visual and sound indication may be provided at all times during operation of the apparatus if the casette is not in its fully engaged position with the plungers.

DESCRIPTION OF THE INVENTION

In this invention, flow controlling apparatus is provided including a separate casette, and a controller member adapted to receive and hold the casette. In accordance with this invention, means for indicating the correct positioning of the casette in the controller member are provided.

Specifically, the position indicating means utilized herein comprises a rotationally movably member, movable in a manner relating to the position of the casette in the controller, and a bearing member, one of said members defining a projection adapted to bear against the other.

An electrical switch is adapted to be opened and closed by the member which carries the projection. A recess in the member which does not carry the projection is adapted to receive the projection in the position of the movable member when the casette is correctly positioned in the controller member.

Alarm means are operated by the switch, with the result that the switch is closed to operate the alarm means when the projection is spaced from the recess, and the switch is open, so that the alarm means does not operate, when the projection is positioned in the recess.

As described above, the casette is movable into its correct position by a rotatable crank, and the relatively movable member comprises a disc carried by the crank, and defining the recess. A stationary member defines the bearing member and projection.

Accordingly, by this invention, the alarm indicating incorrect positioning of the casette sounds at all times during operation of the controller member, except when the projection occupies the recess, which can only take place when the rotatable crank or other casette moving means has been positioned so that the casette is in its correct position for operation.

Referring to the drawings.

Figure 1:
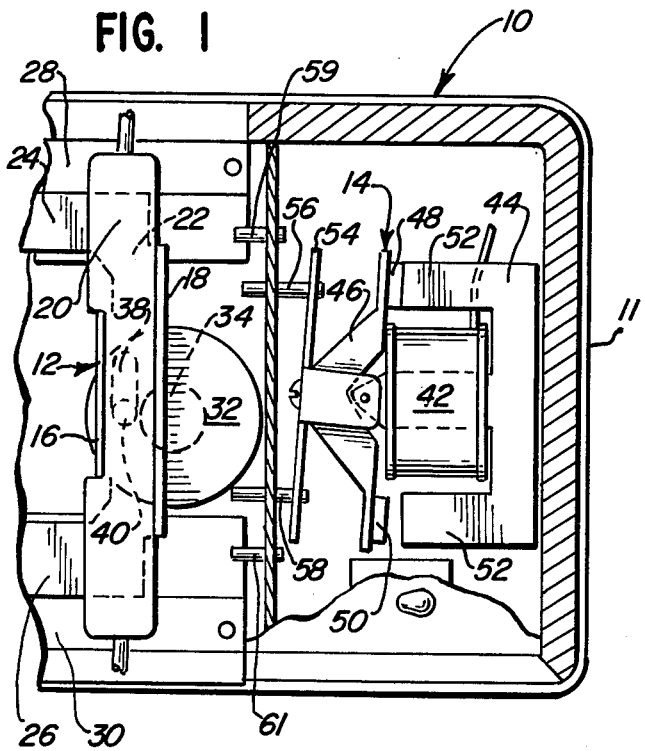
FIG. 1 is an elevational view, with portions broken away, of the flow controlling apparatus of this invention carrying the casette in its position in which the casette is initially installed.
Figure 2:
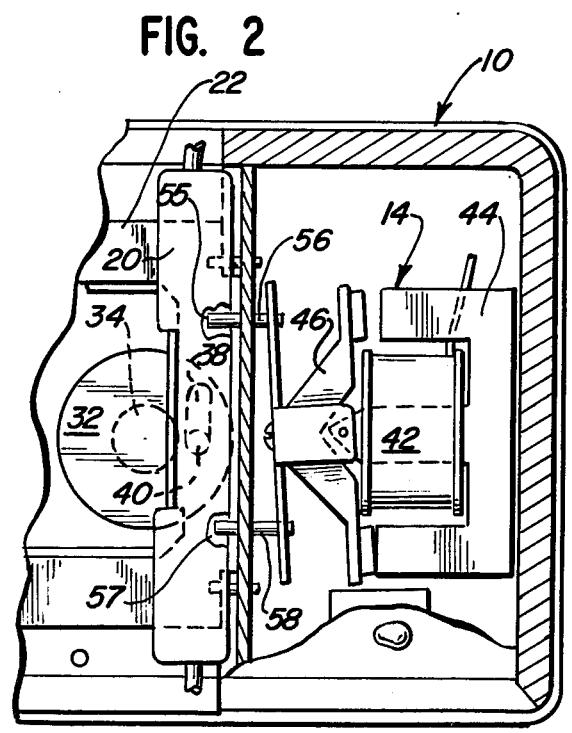
FIG. 2 is an elevational view, similar to FIG. 1, except that the casette has been moved by the crank into engaging relation with the valving plungers of the controller.

Referring to the drawings, FIGS. 1 and 2 show a casette and controller arrangement which is described in detail in my U.S. patent application Ser. No. 878,970, filed Feb. 17, 1978. Controller member 10 comprises a casing 11 for receiving and retaining a casette holding assembly 12 and an electrically controlled valving assembly 14. Casette holding assembly comprises a pair of retaining plates 16, 18 which are proportioned to receive and hold casette 20 in the manner indicated.

Casette 20 may be of the specific design which is currently being sold as the Travenol Infusion Set, for use in a commercially available Travenol Infusion Controller, both of which are sold by Travenol Laboratories of Deerfield, Ill.

The structure of FIGS. 1 and 2 is intended to be basically a schematic representation of the precise structure utilized in those products, with the modifications of this invention being primarily illustrated in FIGS. 3 through 6 of this invention.

Retainer plates 16, 18 serve to orient the casette and retain it in a precise position. Retainer plates 16, 18 form part of a single holder, and connect together through back piece 22, which, in turn, defines a pair of legs 24, 26, which slide on a pair of tracks 28, 30 so that the entire casette 20 and retaining structure are horizontally movable (from the viewpoint of FIG. 1).

Disc 32 is attached to crank 34 defining handle 36 for manual turning of the crank. Disc 32 defines a vertical stud 40, as part of crank 34, while back piece 20 of the casette sliding assembly defines a slot 38 into which stud 40 fits.

Accordingly, as crank 34 is rotated clockwise from the viewpoint of FIG. 1, casette 20, carried in the slide arrangement, is drawn to the right with the stud 40 rising to the top of slot 38 upon 90° of clockwise rotation of disc 32, and then falling again to the bottom of slot 38, as shown in FIG. 2, with 180° of clockwise rotation, which brings casette 20 at the end of the rotation into firm engagement with the valving assembly 14.

As described in the patent application cited above, and as used in the Travenol flow controller system, the valving assembly 14 comprises an electromagnet 42 which is positioned on the middle arm of an E-frame pole piece 44. An armature member 46 is pivotally attached to pole piece 44 in an insulating manner so that it is pivotal back and forth between the positions of FIGS. 1 and 2 to bring magnets 48, 50, which define opposite outwardly extending polarities, into close proximity with the associated arms 52 of E-frame pole piece.

Accordingly, the polarity of the E-frame pole piece 44 can be achieved by alternating the direction of current in the electromagnet coil 42, with the result that armature 46 moves back and forth between its two positions, since E-frame pole piece 44 will assume one magnetic polarity which attracts one of magnets 48, 50 and repels the other, depending upon the variable polarity of the member 44.

Pivotally mounted armature 46 carries a spring member 54 which in turn carries a pair of valving plungers 56, 58, which are adapted to enter apertures 55, 57 of casette 20 as shown in FIG. 2, to press a membrane of casette 20 into flow blocking relation in the inlet orifice and outlet orifice respectively of a metering chamber in a manner known in the prior art and used in the Travenol products identified above.

As armature 46 swings back and forth between its two extremes of rotation, the valve plungers 56, 58 alternatingly enter into and withdraw from flow blocking relation with the metering chamber inlet and outlet of casette 20, so that the frequency of the switching of rotational positions of armature 46 precisely controls the amount of liquid passing through casette 20.

Positioning pins 59, 61 are provided for precise positioning of casette 20.

In accordance with this invention, means for indicating the correct positioning of the casette in the controller member are provided. A rotatably movable member 60 is formed in the shape of a disc and attached to crank 34, generally outside of casing 11. A bearing member 62 is in the form of a leaf spring, attached by bolt 64 to casing 11. A projection 66 is carried by one of members 60, 62, specifically leaf spring 62 in the present embodiment, and is adapted to fit in a recess 68 which is defined in the member which does not carry the projection, i.e., rotatably movable member 60 in this instance.

Leaf spring 62 bears against a switch 70, which may be a microswitch or the like.

Figure 4:
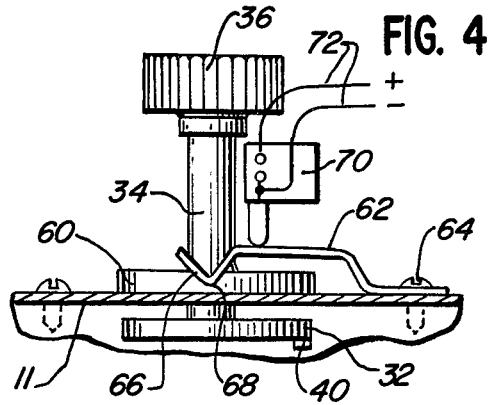
FIG. 4 is a fragmentary plan view of the rotating crank which projects from the back of the controller of FIG. 1, shown in the configuration that corresponds to correct positioning of the casette for operation.

In FIG. 4, the rotational position of crank 34 and movable member 60 is shown to correspond to the configuration of FIG. 2, in which casette 20 is in its proper position to engage plungers 56, 58. In this configuration, projection 66 of leaf spring 62 is positioned in recess 68, to lower leaf spring 62. This has the effect of opening microswitch 70 so that electrical current does not pass through line 72.

Figure 5:
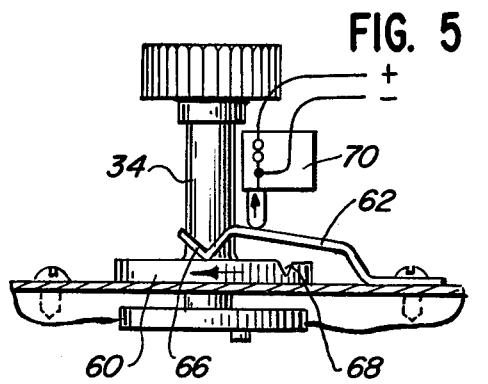
FIG. 5 is a fragmentary plan view similar to FIG. 4, showing a position of the rotatable crank when the casette occupies an inoperative position in the controller.

Whenever crank 34 and movable member 60 are in any other rotational position, for example the rotational position of FIG. 1 which is 180° away from the configuration of FIG. 4, or the intermediate rotational position shown in FIG. 5, projection 66 no longers resides in recess 68, with the result that leaf spring 62 is elevated. The effect of this is to cause microswitch 70 to be closed, allowing electrical current to pass.

Electrical circuitry which may be utilized by controller 10 is disclosed in detail in U.S. Application Ser. No. 878,846, filed Feb. 17, 1978. Alternatively, any conventional electrical circuitry may be used to provide the desired control of valving assembly 14.

Figure 3:
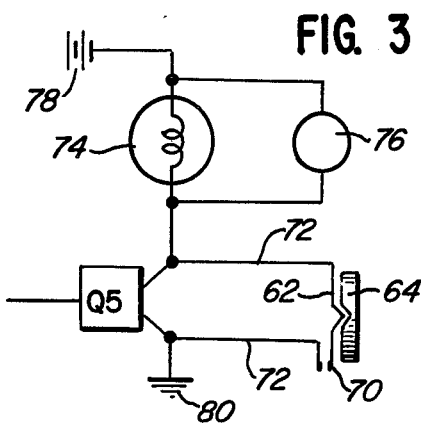
FIG. 3 is a portion of an electrical circuit which may be used in this present invention, showing the circuitry of the alarm system and the switch in accordance with this invention.

FIG. 3 shows a modification of circuitry which may be utilized in this invention. Transistor Q5 receives a pulsed signal, and opens in the event of low battery power, to permit an intermittent pulsing on/off action of light 74 and buzzer 76, powered by battery 78 through a circuit which is grounded at 80. In accordance with this invention, bearing member 62, relatively movable member 64, and switch 70 are connected in parallel relation to transistor Q5 between battery 78 and ground 80.

Accordingly, when the projection 66 does not reside in recess 68, switch 70 is closed, permitting a constant application of power to light 74 and 76.

Thus, light 74 and buzzer 76 provide a selective indication of two problems in the device of this invention, with a pulsating signal implying a low battery as is conventional, and a constant signal indicating that the casette 20 and crank 34 are not properly positioned for operation.

Figure 6:
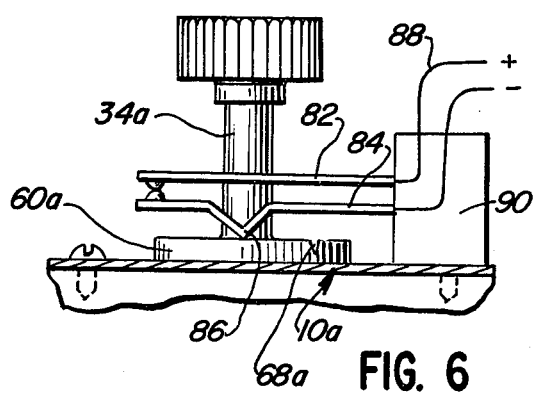
FIG. 6 is a fragmentary plan view of an alternate configuration to that shown in FIG. 5.

Referring to FIG. 6, crank 34a and rotatably movable member 60a having recess 68a are mounted on the housing of a controller 10a in a manner analogous to the previous embodiment. In this present embodiment, a pair of leaf spring terminals 82, 84 are provided, being normally in spaced, electrically non-conducting relation to each other, when projection 86 rests in recess 68a, so that no electrical current flows through lines 88.

However, in the position shown in FIG. 6 when projection 86 does not rest in recess 68a, which indicates improper positioning of the casette and crank 34a for operation of the device, an electrical connection is made between leaf springs 82, 84 for continuous operation of light 74 and buzzer 76.

Leaf springs 82, 84 are held by block 90, and may be of conventional construction.

Additionally, brackets may be attached to arms 52 of the pole piece 44 and used to engage the rear surface of armature 46 in a rotating position of the armature to prevent magnets 48, 50 from coming into contact with arms 52, to reduce the noise of operation of valving assembly 14 and to prevent shock against magnets 48, 50.

Accordingly, improved safety and convenience of the operation in the flow control casette and controller of this invention is provided, with positive assurance that the casette is properly positioned for effective operation for controlling the flow, for example, of parenteral solution to a patient in precise, predetermined volumes.

The above has been offered for illustrative purposes only, and is not intended to limit the invention of this application, which is as defined in the claims below.

That which is claimed is:

1. In flow controlling apparatus including a separate casette defining a liquid flow path, and a controller adapted to receive and hold said casette, the improvement comprising, in combination:

means for indicating the correct positioning of the casette in the controller, said means comprising: a rotationally movable member, movable in a manner relating to the position of the casette, and a bearing member, one of said members defining a projection adapted to bear against the other member; an electrical switch adapted to be opened and closed by one of said members; a recess defined in the member which does not carry the projection, said recess being adapted to receive the projection in the position of the rotationally movable member when the casette is correctly positioned in the controller; and alarm means operated by said switch, whereby said switch is closed to operate said alarm means when the projection of the movable member is spaced from said recess, and said switch is open when said projection is positioned in the recess.

2. The apparatus of claim 1 in which said casette is moved into its correct position by a rotatable crank, said rotationally movable member comprising a disc carried by said crank and defining said recess.

3. The apparatus of claim 2 in which said projection is an integral part of said bearing member.

4. The apparatus of claim 3 in which said switch defines terminals which are connected in parallel in a circuit with a transistor modulating a pulsing signal as a low battery voltage indicator, said circuit including said alarm means, whereby said alarm means operates in pulsed manner upon sensing of a low battery, and said alarm operates continuously when said movable member is out of the position of correct casette emplacement.

5. The apparatus of claim 4 in which said bearing member is a flexible, flat spring member.

6. The flow controlling apparatus of claim 1 which is adapted for use with a flow controller for the delivery of parenteral solution to a patient.

* * * * *